(12) United States Patent
Rolston

(10) Patent No.: US 10,753,832 B2
(45) Date of Patent: Aug. 25, 2020

(54) SPEED LOOP FOR TAKE-OFF AND RETURN BY SINGLE PIPELINE PROBE

(71) Applicant: Mustang Sampling LLC, Ravenswood, WV (US)

(72) Inventor: Claude A. Rolston, St. Marys, WV (US)

(73) Assignee: Mustang Sampling, LLC, Ravenswood, WV (US)

( * ) Notice: Subject to any disclaimer, the term of this patent is extended or adjusted under 35 U.S.C. 154(b) by 270 days.

(21) Appl. No.: 15/748,679

(22) PCT Filed: Sep. 2, 2016

(86) PCT No.: PCT/US2016/050179
§ 371 (c)(1),
(2) Date: Jan. 30, 2018

(87) PCT Pub. No.: WO2017/058465
PCT Pub. Date: Apr. 6, 2017

(65) Prior Publication Data
US 2019/0003932 A1    Jan. 3, 2019

Related U.S. Application Data

(60) Provisional application No. 62/235,107, filed on Sep. 30, 2015.

(51) Int. Cl.
*G01N 1/22* (2006.01)
*G01N 1/10* (2006.01)
(Continued)

(52) U.S. Cl.
CPC ............. *G01N 1/2035* (2013.01); *G01N 1/14* (2013.01); *G01N 1/42* (2013.01); *G01N 1/44* (2013.01);
(Continued)

(58) Field of Classification Search
CPC .................. F04D 17/16; G01N 33/009; G01N 2001/245; G01N 1/24; G01N 1/2273;
(Continued)

(56) References Cited

U.S. PATENT DOCUMENTS 4,594,903 A * 6/1986 Johnson ................... G01N 1/14
422/283
5,018,395 A * 5/1991 Hickox ................... F04D 17/16
73/864.34

(Continued)

FOREIGN PATENT DOCUMENTS

RU    2326365 C1    6/2008

OTHER PUBLICATIONS

European Patent Office, Application No. 16852286.0, Extended Search Report, dated May 14, 2019.
(Continued)

*Primary Examiner* — Brandi N Hopkins
(74) *Attorney, Agent, or Firm* — Cahn & Samuels, LLP

(57) ABSTRACT

A sample take-off system incorporating a small volume pump with a speed loop for pressurizing excess extracted sample for return into the process stream using a single multi-channel probe for both take-off and return of the excess extracted sample is illustrated and described.

15 Claims, 2 Drawing Sheets

(51) Int. Cl.
- *G01N 1/02* (2006.01)
- *G01N 1/20* (2006.01)
- *G01N 1/14* (2006.01)
- *G01N 33/00* (2006.01)
- *G01N 33/22* (2006.01)
- *G01N 1/44* (2006.01)
- *G01N 1/42* (2006.01)
- *G01N 1/24* (2006.01)

(52) U.S. Cl.
CPC ....... *G01N 33/0011* (2013.01); *G01N 33/225* (2013.01); *G01N 1/24* (2013.01); *G01N 2001/105* (2013.01); *G01N 2001/2064* (2013.01)

(58) Field of Classification Search
CPC ....... G01N 2001/2276; G01N 33/0011; G01N 1/2035; G01N 1/42; G01N 2001/105; G01N 1/14; G01N 33/225; G01N 30/30; G01N 2030/326; G01N 30/32; G01N 2030/025; G01N 33/0016; G01N 30/06; G01N 30/26; G01N 33/22; G01N 1/44; G01N 30/88; G01N 30/062
See application file for complete search history.

(56) References Cited

U.S. PATENT DOCUMENTS

| | | |
|---|---|---|
| 5,317,932 A | 6/1994 | Westlake et al. |
| 7,162,933 B2 | 1/2007 | Thompson et al. |
| 7,484,404 B2 | 2/2009 | Thompson et al. |
| 8,056,399 B2 | 11/2011 | Thompson et al. |
| 9,285,299 B2 | 3/2016 | Thompson |
| 2005/0087237 A1 | 4/2005 | O'dougherty et al. |
| 2013/0036800 A1 | 2/2013 | Mohajer |
| 2014/0169993 A1* | 6/2014 | Berzak ............... B01D 8/00 417/401 |
| 2015/0000426 A1* | 1/2015 | Rolston ............. G01N 33/0016 73/863.11 |
| 2017/0089809 A1* | 3/2017 | Rolston ............. G01N 33/0011 |

OTHER PUBLICATIONS

English Abstract of RU 2326365.
International Search Report from PCT for International Application No. PCT/US2016/050179 dated Nov. 8, 2016.

\* cited by examiner

SPEED LOOP FOR TAKE-OFF AND RETURN BY SINGLE PIPELINE PROBE

CROSS REFERENCE TO RELATED APPLICATIONS

This application is a 371 national stage application from international application PCT/US2016/050179 filed on Sep. 2, 2016 and claims priority to U.S. provisional patent application Ser. No. 62/235,107 filed on Sep. 30, 2015.

This PCT international application claims priority of U.S. application Ser. No. 15/252,686 filed Aug. 31, 2016 and U.S. provisional application Ser. No. 62/235,107 filed Sep. 30, 2015.

TECHNICAL FIELD

This invention relates to a system and method of establishing a speed loop that uses a single pipeline probe for sample take-off and fast-loop return of excess extracted sample to the pipeline process stream. The invention is particularly useful in the case of a low pressure gas source. A further aspect of the invention is to associate the speed loop with a pump to boost the pressure of low pressure sample gas to offset the take-off vacuum (i.e. suction pressure) and permit reinjection of excess sample fluid into the pipeline. Use of the invention avoids emissions by recirculating unused take-off fluid back into the pipeline source.

BACKGROUND

In the gas processing industry, excess sample fluid, often referred to as "boil off gas" or "BOG", is disposed of by flaring or other disposal means. When provisions are made to avoid flaring, such as by recirculating excess extracted sample to the take-off source or pipeline, sample take-off and return of unused take-off fluids are typically carried out by using a first take-off probe and a second return probe. The addition of a discrete pathway and the second return probe for reinjection, particularly in the case of a highly expandable and even explosive fluid such as natural gas, adds additional requirements for system equipment, installation, and maintenance. The use of such additional equipment also presents further opportunities for leakage and/or system failure. Moreover, in cases of cryogenic fluid sampling, such as Liquid Natural Gas (LNG), conventional design requires the sample extraction probe to be located close to the sample vaporizer and conditioner so as to avoid issues resulting from pre-vaporization and deadheading.

A system that allows for reinjection of unused take-off fluids into the pipeline source without the need for additional equipment, installation, and/or maintenance requirements to the system, such as requirements associated with having a discrete fluid pathway through a second return probe, would be useful in overcoming traditional problems associated with conventional system designs in the gas processing industry, for example, avoiding leakage and/or system failures that result from the use of unnecessary system components.

SUMMARY OF THE INVENTION

It is an object of the present invention to overcome the shortcomings of the existing art.

It is another object of the present invention in certain embodiments to provide a speed loop reinjection system using a single pipeline probe for sample take-off and fast-loop return of excess extracted sample.

Another object of the invention in certain embodiments is to boost the pressure of a low pressure sample gas to permit reinjection of excess extracted sample fluid into the pipeline.

A further object of the invention in certain embodiments is to recirculate unused sample take-off fluid back into the pipeline source so as to minimize waste and emissions generated during sample processing.

Yet another object of the present invention is to minimize equipment, installation, and/or maintenance requirements to the system by excluding the use of unnecessary components from the system.

These and other objects are satisfied by a sample probe system for highly expandable and explosive fluid sample extraction from and reinjection to a fluid sample source, comprising: an elongated unitary stainless steel sample extraction probe having a fluid sample extraction port, an extracted fluid sample exit port, a first extracted fluid communication channel extending generally axially in a direction of elongation of the sample extraction probe for a first select length sufficient to extend between the fluid sample extraction port and the extracted fluid sample exit port, the sample probe defining a discrete return fluid sample reinjection input integrated in the unitary stainless steel body, a return fluid sample reinjection outlet, and a second reinjection fluid communication channel extending axially for a second select length generally parallel to at least a portion of the first extracted fluid communication channel and offset from the first extracted fluid communication channel, the first extracted fluid communication channel establishing fluid communication of a first select length between the fluid sample source and the extracted fluid sample exit port and the second reinjection fluid communication channel defining a second select length extending a select axial distance along the extraction probe body; a sample take-off line in fluid communication with the extracted fluid sample exit port; a sample return line connected to the sample take-off line and in fluid communication with the return fluid sample reinjection outlet; and, a pump disposed along the sample return line downstream of the sample take-off line and upstream of the return fluid sample reinjection outlet, the pump for increasing the pressure of return fluid sample in the sample return line to pressurize fluid sample passing therethrough to provide a speed loop reinjection system.

The invention provides a further embodiment to any of the previous embodiments to the foregoing embodiment characterized in that the sample probe defines a unitary structure and the first select length corresponds to the entire length of elongation of the probe and the second select length is less than the first select length.

The invention provides another embodiment to any of the previous embodiments characterized in that the sample reinjection outlet is axially displaced from the fluid sample extraction port.

The invention provides another embodiment to any of the previous embodiments further characterized by a sample conditioning fluid conveying line connected to both the sample take-off line and the sample return line.

The invention provides another embodiment to any of the previous embodiments characterized in that the pump is disposed in-line with the reinjection line downstream of the first channel and of sample conditioning equipment.

The invention provides in another embodiment to any of the previous embodiments characterized in that the pump is a metering pump disposed in-line in the sample return line.

The invention provides in another embodiment to any of the previous embodiments characterized in that the probe is generally cylindrical and the sample reinjection outlet laterally directed normal to the direction of elongation of the probe.

The invention provides in another embodiment to any of the previous embodiments characterized in that the pump is a cryogenic pump.

The foregoing and still other objects of the invention are satisfied by a multi-channel sample take-off and return probe for single probe speed loop reinjection of a highly expandable and explosive fluid sample from an associated chamber, comprising: a sample probe defining a unitary stainless steel body having an axial length sufficient to extend into the associated fluid chamber and defining a first axially extending channel and a second axially extending channel formed in the stainless steel body, the first axially extending channel establishing a fluid communication having a first select length for passing the fluid from the fluid chamber through the sample probe and the second axially extending channel having a second select length extending a select axial distance along the probe; a sample take-off line in fluid communication with the first axially extending channel; and, a sample return line connected to the sample take-off line and in fluid communication with the second axially extending channel, the second axially extending channel having a return discharge port displaced from a sample take-off to minimize fluid flow disturbance in the fluid chamber from a reinjected fluid.

The invention provides in a further embodiment to the foregoing embodiment characterized in that the second channel further has at least one laterally disposed discharge port.

The invention provides in another embodiment to the any of the previous two embodiments characterized in that the second channel further has at least one laterally disposed entry port.

The invention provides in another embodiment to the foregoing embodiment characterized in that the entry port is threaded to removably secure the sample return line to the probe.

The invention provides in another embodiment to the any of the previous two embodiments characterized in that the second channel is sealed above the entry port by a welding plug.

The invention provides in another embodiment to the any of the previous five embodiments further characterized by a take-off port to removably secure the take-off line to the probe.

The invention provides in another embodiment to the any of the previous six embodiments further characterized by at least one fluid sample extraction port disposed along the first channel.

The invention provides in another embodiment to the any of the previous seven embodiments further characterized by an integrated radially extending flange for removable mounting of the probe to the fluid chamber.

The invention provides in a further embodiment to the foregoing embodiment characterized in that the probe is mounted to the fluid chamber by bolting the flange through cooperatively positioned bolt holes.

Yet other objects of the invention are satisfied by a method of using a multi-channel single probe unused extracted highly expandable and explosive sample fluid speed loop reinjection system incorporating a pump for pressurizing the unused extracted sample fluid for reinjection thereof into the extracted sample fluid source where the probe defines an integrated unitary stainless steel body including includes an extracted sample fluid pathway and a unused highly expandable and explosive fluid sample reinjection pathway, comprising the steps of: extracting a highly expandable and explosive fluid from a fluid source; communicating the fluid through the extracted sample fluid pathway; returning unused extracted sample fluid through unused fluid sample reinjection pathway; increasing the pressure of the unused extracted sample fluid in the unused fluid sample reinjection pathway; and reinjecting the fluid into the extracted sample fluid source.

The invention provides in another embodiment to the foregoing embodiment further characterized by the step of displacing the unused extracted sample fluid to minimize fluid flow disturbance in the fluid source.

The invention provides in another embodiment to the any of the previous two embodiments further characterized by the step of communicating the fluid to a downstream sample conditioner and an analyzer.

The invention provides in another embodiment to the foregoing embodiment further characterized by the step of pressurizing the fluid with a pump disposed downstream of a probe but upstream of the sample conditioner.

The invention provides in a further embodiment to the foregoing embodiment characterized in that the pressure of the fluid is higher than a suction pressure of the fluid source.

The invention provides in another embodiment to any of the previous two embodiments characterized in that the pump is an in-line pump.

In short, the invention contemplates a speed loop for sample take-off and return by a single pipeline probe using a pump to increase the pressurize of any excess extracted fluid in a speed loop return line for reinjection into the extracted fluid source by overcoming, for example, suction pressure generated by fluid flow through a pipeline.

The invention still further contemplates a combination of elements characterized by a multi-channel sample take-off and return probe, having a discharge port axially displaced from an entry port to minimize fluid flow disturbance in the pipeline process stream.

The present invention provides for use of a single pipeline probe for both take-off and sample return by incorporating a speed loop with the probe. The speed loop preferably is associated with a pump, which is preferably a small volume cryogenic pump located downstream of the probe but upstream of sample conditioning equipment to increase the pressure of the fluid in the speed loop return line and, more particularly, to increase the associated fluid discharge pressure from the probe.

In one embodiment, the probe is characterized by a unitary structure with a welded radially extending flange featuring threaded holes for bolting the structure to an underlying flange nozzle. The probe includes two discrete fluid passages in which a first sample take-off bore extends axially through the entire length of the probe and a second return bore extends axially for a select distance from above the bottom of the sample take-off bore to a select distance near the top of the probe.

The return bore includes a return input port and a return discharge port. Preferably, the return input port is disposed laterally relative to the return bore at a select length below the top of the probe and above the flange. The return input port is preferably threaded to permit removably secure attachment to the connected speed loop return line. The return discharge port is likewise preferably disposed laterally relative to the return bore but is disposed at a position along the length of the probe selected to provide for return of excess extracted sample into the pipeline. The return discharge port is further sufficiently separated from the take-off bore so as not to disturb the flow or composition of the sample take-off fluid.

The bores described above may be machined using a single stainless steel cylinder. The take-off bore is drilled the entire axial length of the cylinder and features a threaded taper at the top end fabricated according to appropriate specifications, for example, National Pipe Thread (NPT). The return bore is preferably drilled parallel to the take-off bore from the top end of the cylinder to a select depth that is less than the cylinder's axial length. The return input and return discharge ports are then drilled laterally to meet the return bore. The return input port is threaded and the top of the return bore is sealed by welding. The flange is then welded to the cylinder at an axial position along the probe body between the return input port and the return discharge port.

The present invention also contemplates pressure variability based on the particular composition of the subject fluid. Persons having ordinary skill in the art recognize that any given application would vary with the particular make-up of the sampled fluid, as for example, cryogenic LNG or non-cryogenic NGL. Adjusting the requirements for a particular fluid based on the source's composition and phase characteristics, which are readily determinable by convention through individual phase analysis, increases fluid homogeneity, minimizes sample phase separation, and promotes sample return by avoiding deadheading with respect to the speed loop.

The pump used for boosting the pressure of the excess extracted sample may be any off-the-shelf centrifugal, impeller, or magnetic or even pneumatic small volume pump qualified for LNG or NGL use.

In this detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein, the terms "comprises," "comprising," "includes," "including," "has," "having", "characterized", or any other variation thereof, are intended to cover a non-exclusive inclusion. For example, a process, method, article, or apparatus that is characterized by a list of features is not necessarily limited only to those features but may include other features not expressly listed or inherent to such process, method, article, or apparatus.

For definitional purposes and as used herein "connected" includes physical, whether direct or indirect, affixed or adjustably mounted, as for example, the sample probe includes a take-off port connected to a sample take-off line. Thus, unless specified, "connected" is intended to embrace any operationally functional connection.

As used herein, the term "excess extracted sample" connotes a volume of take-off fluid exceeding a minimum intake requirement for sample analysis.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein, the term "speed loop" refers to a fluid transmission path originating at sample take-off and terminating at a point of fluid return to the process stream.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

As used herein "suction pressure" means the pressure of the fluid in the associated pipeline, which may be as low as, for example, ambient atmospheric pressure.

In the following description, reference is made to the accompanying drawings, which are shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION OF THE DRAWINGS

Figure 1:
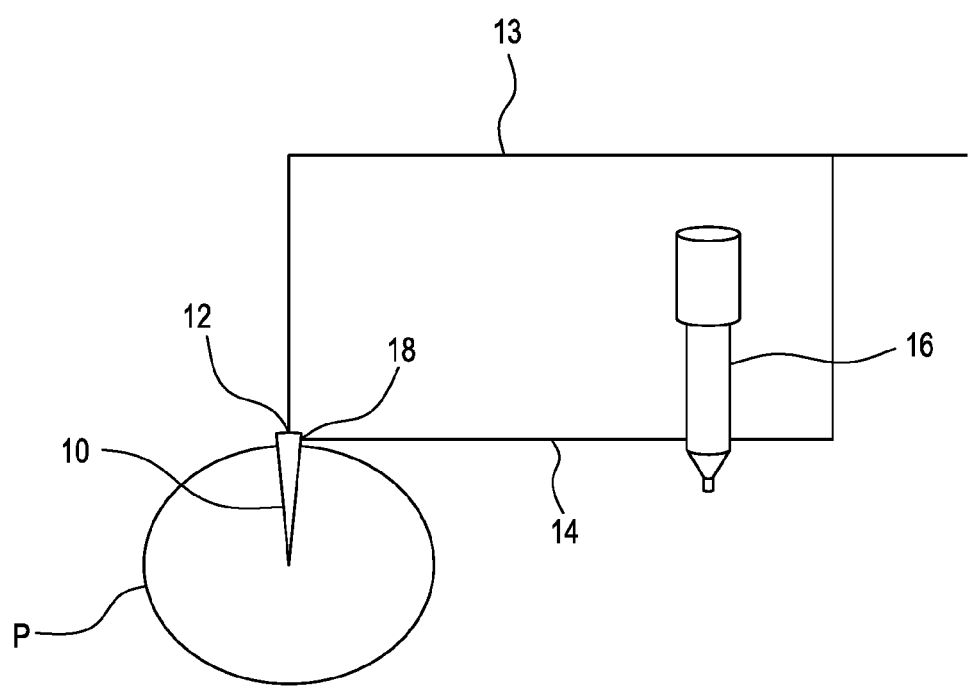
FIG. 1 is a schematic of a single probe speed loop take-off and return system according to an embodiment of the invention.
Figure 2:
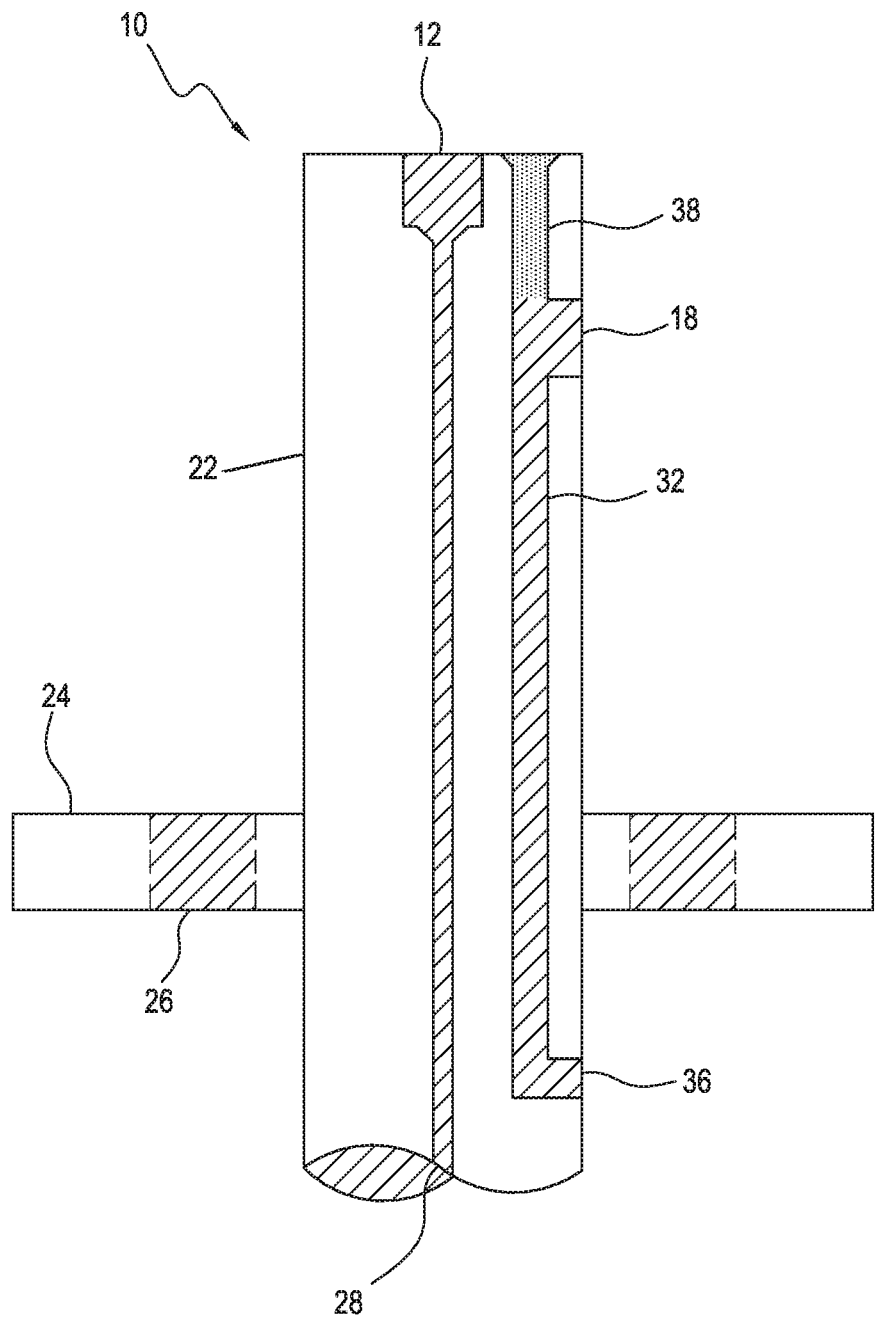
FIG. 2 illustrates a sample probe according to an embodiment of the invention.

FIGS. 1 and 2 illustrate a pipeline P having a sample probe 10 mounted therein. The sample probe 10 includes a take-off port 12 connected to a sample take-off line 13. Disposed at a point along the take-off line 13 and downstream of sample conditioning and/or analyzer equipment is a junction that forms a speed loop sample return line 14. The speed loop return line 14 features an in-line small volume pump 16 to increase the pressure of the returning excess extracted sample fluid prior to injection of the fluid into the return input port 18 of the sample probe 10.

FIG. 2 illustrates details of an embodiment of an integrated, unitary sample probe 10 in accordance with the invention. The probe 10 features a stainless steel cylindrical body 22 with a length selected to project above a mounting flange (not illustrated) located on an underlying pipeline P. The probe 10 is removably secured to the pipeline mounting flange by direct bolting of probe flange 24 via cooperatively positioned bolt holes 26. The cylindrical body 22 is of a length to project to about the axis of the underlying pipeline P and includes a take-off bore 28 extending the entire axial length of the probe 10 and terminating at the top of the probe 10 with a take-off port 12 that is preferably threaded. An axially aligned return channel 32 parallels, in part, the take-off bore 28.

The return channel 32 includes a return input port 18, disposed between the top of the probe 10 and the probe flange 24, incorporating a threaded female connector for connecting to a return line 14 from the sample take-off system. The return channel 32 terminates with a return discharge port 36, disposed a select distance below the probe flange, for discharge of excess extracted sample take-off into the pipeline P. The return input and discharges ports (18, 36) are preferably parallel and disposed laterally relative to the return channel 32.

Notably, the return channel 32 is formed by drilling a bore from the top of the probe 10 to a select distance below the probe flange 24. The upper portion of the bore is then sealed above the return input port 18 by a welding plug 38.

While not intended to be limiting as to relative parameters, in one embodiment of the invention the take-off bore 28 has a diameter of 0.125 in. (0.3175 cm) and the return channel 32 has a diameter of 0.23 in. (0.5842 cm). Likewise not intended to be limiting, in one embodiment of the invention the return input port 18 is disposed 3 in. (7.62 cm) above probe flange 24, in the cylindrical body 22 which itself extends 4.54 in. (11.5316 cm) above the probe flange 24, and the return discharge port 36 is disposed 1.125 in. (2.8578 cm) below the probe flange 24, in the cylindrical body 22.

The invention has been disclosed in the foregoing specification. It is understood by those skilled in the art that many modifications and embodiments of the invention will come to mind to which the invention pertains, having benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description of the invention.

INDUSTRIAL APPLICABILITY

The invention is useful for low pressure gas sampling systems by providing a single sample probe for fluid sample extraction from and reinjection to a fluid sample source for speed loop reinjection of unused extracted sample fluid into the fluid source with a fluid pump associated with the speed loop return.

I claim:

1. A sample probe system for highly expandable and explosive fluid sample extraction from and reinjection to a fluid sample source, comprising:
    an elongated unitary stainless-steel sample extraction probe having a fluid sample extraction port, an extracted fluid sample exit port, a first extracted fluid communication channel extending generally axially in a direction of elongation of the sample extraction probe for a first select length sufficient to extend between the fluid sample extraction port and the extracted fluid sample exit port, the sample probe defining a discrete return fluid sample reinjection input integrated in the unitary stainless-steel body, a return fluid sample reinjection outlet, and a second reinjection fluid communication channel extending axially for a second select length generally parallel to at least a portion of the first extracted fluid communication channel and offset from the first extracted fluid communication channel,
    the first extracted fluid communication channel establishing fluid communication of a first select length between the fluid sample source and the extracted fluid sample exit port and the second reinjection fluid communication channel defining a second select length extending a select axial distance along the extraction probe body;
    a sample take-off line in fluid communication with the extracted fluid sample exit port;
    a sample return line connected to the sample take-off line and in fluid communication with the return fluid sample reinjection outlet; and,
    a pump disposed along the sample return line downstream of the sample take-off line and upstream of the return fluid sample reinjection outlet, the pump for increasing the pressure of return fluid sample in the sample return line to pressurize fluid sample passing therethrough to provide a speed loop reinjection system.

2. The system of claim 1 where the sample probe body defines a unitary cylindrical structure and the first select length corresponds to the entire length of elongation of the probe and the second select length is less than the first select length.

3. The system according to claim 1 where the sample reinjection outlet is axially displaced from the fluid sample extraction port.

4. The system according to claim 1 where the pump is a metering pump disposed in-line in the sample return line.

5. The system according to claim 4 where the pump is a cryogenic pump.

6. The system according to claim 1 where the probe is generally cylindrical and the sample reinjection outlet is laterally directed normal to the direction of elongation of the probe.

7. A multi-channel sample take-off and return probe for single probe speed loop reinjection of a highly expandable and explosive fluid sample from an associated chamber, comprising:
    a sample probe defining a unitary stainless steel body having an axial length sufficient to extend into the associated fluid chamber and defining a first axially extending channel and a second axially extending channel formed in the stainless steel body, the first axially extending channel establishing a fluid communication having a first select length for passing the fluid from the fluid chamber through the sample probe and the second axially extending channel having a second select length extending a select axial distance along the probe;
    a sample take-off line in fluid communication with the first axially extending channel; and,
    a sample return line connected to the sample take-off line and in fluid communication with the second axially extending channel, the second axially extending channel having a return discharge port displaced from a sample take-off to minimize fluid flow disturbance in the fluid chamber from a reinjected fluid.

8. The multi-channel sample take-off and return probe according to claim 7 where the second channel further has at least one laterally disposed discharge port.

9. The multi-channel sample take-off and return probe according to claim 7 where the second channel has at least one laterally disposed entry port.

10. The multi-channel sample take-off and return probe according to claim 9 where the entry port is threaded to removably secure the sample return line to the probe.

11. The multi-channel sample take-off and return probe according to claim 10 further comprising an integrated radially extending flange for removable mounting of the multi-channel sample take-off and return probe to the fluid chamber.

12. A method of using a multi-channel single probe unused extracted highly expandable and explosive sample fluid speed loop reinjection system incorporating a pump for pressurizing the unused extracted sample fluid for reinjection thereof into the extracted sample fluid source where the probe defines an integrated unitary stainless steel body including an extracted sample fluid pathway and a unused highly expandable and explosive fluid sample reinjection pathway, comprising the steps of:
 a) extracting a highly expandable and explosive fluid from a fluid source;
 b) communicating the fluid through the extracted sample fluid pathway;
 c) returning unused extracted sample fluid through unused fluid sample reinjection pathway;
 d) increasing the pressure of the unused extracted sample fluid in the unused fluid sample reinjection pathway; and
 e) reinjecting the fluid into the extracted sample fluid source.

13. The method according to claim 12 further comprising the step of displacing the unused highly expandable and explosive extracted sample fluid to minimize fluid flow disturbance in the fluid source.

14. The method according to claim 12 further comprising the step of increasing the pressure of the highly expandable and explosive fluid to be higher than a suction pressure of the fluid source.

15. The method according to claim 12 further comprising the step of locating the pump in the reinjection pathway.

* * * * *